United States Patent [19]

Tsuchida et al.

[11] Patent Number: 5,092,333
[45] Date of Patent: Mar. 3, 1992

[54] CATHETER ACCOMMODATING ELECTRICAL WIRES

[76] Inventors: Kouji Tsuchida; Yoshio Ishitsu; Shigekazu Sekii, all of Fuji, Japan

[21] Appl. No.: 449,937

[22] Filed: Dec. 21, 1989

[30] Foreign Application Priority Data

Jun. 25, 1987 [JP] Japan .................. 62-158142

[51] Int. Cl.$^5$ ............................. A61B 5/04
[52] U.S. Cl. .................. 128/642; 128/786; 128/715
[58] Field of Search .......... 128/642, 784–786, 128/633, 637, 664–667, 673, 675, 692, 715, 773, 775, 778, 780; 604/21

[56] References Cited

U.S. PATENT DOCUMENTS 3,669,095  6/1972  Kobayashi et al. .............. 128/659
4,823,805  4/1989  Wojcik ............................ 128/736

FOREIGN PATENT DOCUMENTS 131389      1/1933   Fed. Rep. of Germany ...... 128/784
WO81/03614  6/1981   World Int. Prop. O. .
0024913     8/1980   European Pat. Off. .
49-25502    7/1974   Japan .
52-13871    4/1977   Japan .
WO80/02801  12/1980  World Int. Prop. O. .......... 128/786

*Primary Examiner*—Francis Jaworski
*Assistant Examiner*—Scott R. Akers
*Attorney, Agent, or Firm*—Frishauf, Holtz, Goodman & Woodward

[57] ABSTRACT

A catheter accommodating an electrical wire in the longitudinal direction thereof, wherein an enlargement is provided in at least part of its cavity, and an excess length of wire respect to the catheter in the unstretched state is accommodated slack in the enlargement.

10 Claims, 3 Drawing Sheets

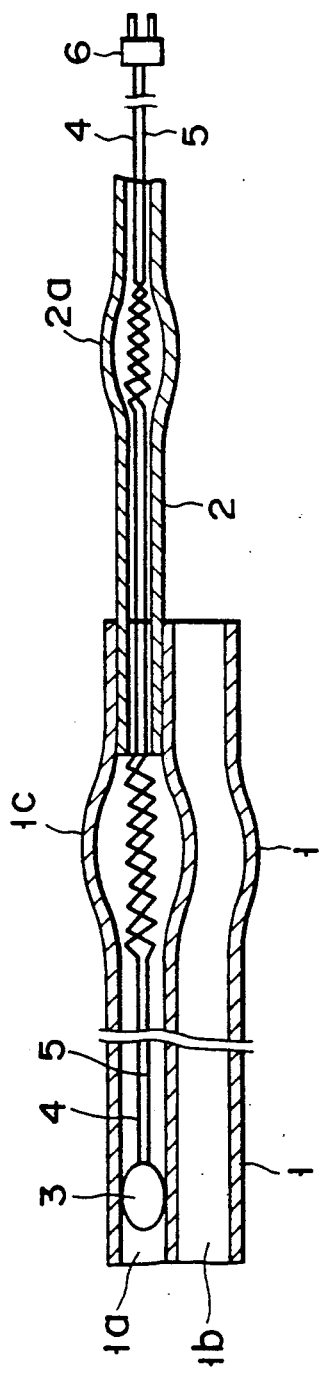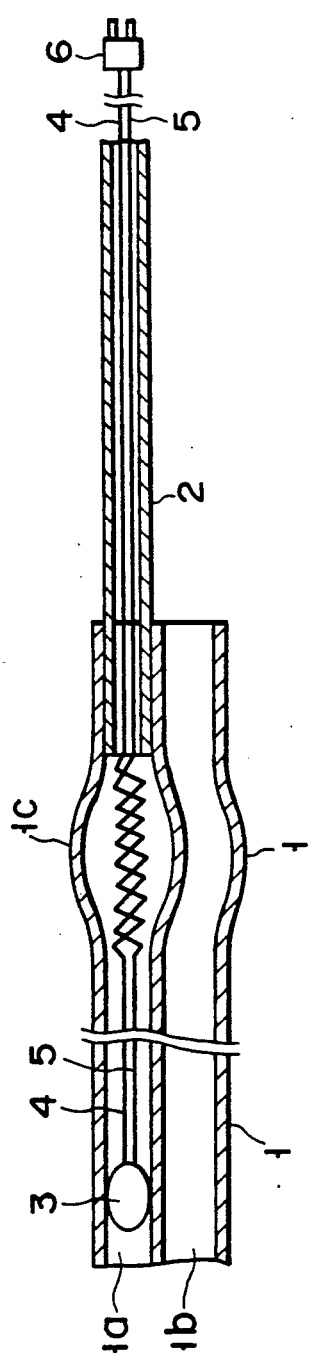

CATHETER ACCOMMODATING ELECTRICAL WIRES

TECHNICAL FIELD

The present invention relates to a catheter accommodating electrical wires to obtain various intracorporeal information from a distal end thereof in the form of electrical signals.

BACKGROUND ART

At present, various kinds of electrical elements are inserted into the ends of catheters for various medical purposes. The signals from these elements are transmitted to various devices by means of electrical wires arranged in the catheter body and in extension tubes which are connected to it.

In order to insert these catheters easily into the body, they are usually made of a relatively flexible material such as soft plastic, and they can be easily stretched by an external stress or the action of heat. The electrical wires, on the other hand, generally consist of metallic material, and they are capable of much less elongation than the catheter body by an external stress or heat. When the catheter is carelessly stretched during handling, therefore, these wires easily break.

Various methods have been proposed in the prior art to prevent the breaking of electrical wires in such catheters. Such methods include, for example, increasing the outer diameter of the wires to thereby increase their breaking strength; adding additives to the materials of the wires to thereby increase their breaking strength; or coiling the wires throughout the catheter body and the whole of the extension tubes.

However, the technique of increasing the outer diameter of the wires cannot be applied to catheters of a small diameter. The addition of additives to wires does not provide sufficient strength for catheters of a small outer diameter, and is also undesirable as it increases the electrical resistance which interferes with signal transmission performance. Coiling the wires throughout the whole length of the catheter is practically impossible if the internal cavity is narrow, or the catheter is too long.

DISCLOSURE OF INVENTION

The present invention aims to provide a catheter accommodating electrical wires wherein the wires do not break even if the catheter body and extension tubes are carelessly stretched, and which is fully applicable even to catheters with narrow and long internal cavities.

To solve the above problems, the present invention provides an enlargement at at least part of the catheter body, extension tube or both. In this enlargement, that excess portion of the electrical wire is accommodated slack which corresponds to a stretchable length of the catheter body, etc., under an external stress.

More specifically, this invention provides a catheter accommodating an electrical wire or wires wherein the wire is arranged in its cavity along the longitudinal direction thereof, and wherein in that an enlargement is provided in at least part of the cavity, and an excess length of electrical wire with respect to the unstretched length of said catheter is accommodated slack in the enlargement.

The length of excess wire accommodated in the above-mentioned enlargement can be such that, depending on the material of the catheter and the extension tubes and the uses to which they are to be put, there is no risk of the wire breaking in normal use, and it is preferably not less than 10% of the permitted elongation of the catheter.

There is moreover no special restriction on the shape of the excess wire accommodated in the enlargement, and it may for example be in the form of a coil or zigzag.

The maximum diameter of the enlargement should be such as to be able to accommodate the excess wire portion, and preferably not less than 1.5 times the maximum diameter of other parts of the cavity. Further, the length of the enlargement may be suitably chosen to suit the length of the excess wire portion and the diameter of the enlargement.

In the electrical wire-accommodating catheter of the present invention, therefore, even if the catheter body is or the extension tube or tubes are carelessly stretched by an external force, etc., the slack wire in the enlargement is merely stretched at the same time, and external stress is not applied to the conductor in other parts of the cavity. In this catheter, therefore, there is no risk of a broken wire. Further, as the excess wire corresponding to the elongation of the catheter is accommodated in only part of the catheter body or extension tubes, the invention can also be applied to catheters having a narrow internal cavity.

BRIEF DESCRIPTION OF THE DRAWINGS

This invention will become clear from the description of examples with reference to the drawings.

FIG. 1 is a sectional view of the main parts of an electrical wire-accommodating catheter of the present invention.

FIG. 2 is a sectional view of the main parts of an electrical wire-accommodating catheter according to another embodiment of the present invention having an enlargement in part of the catheter body.

BEST MODE OF CARRYING OUT THE INVENTION

Figure 3:
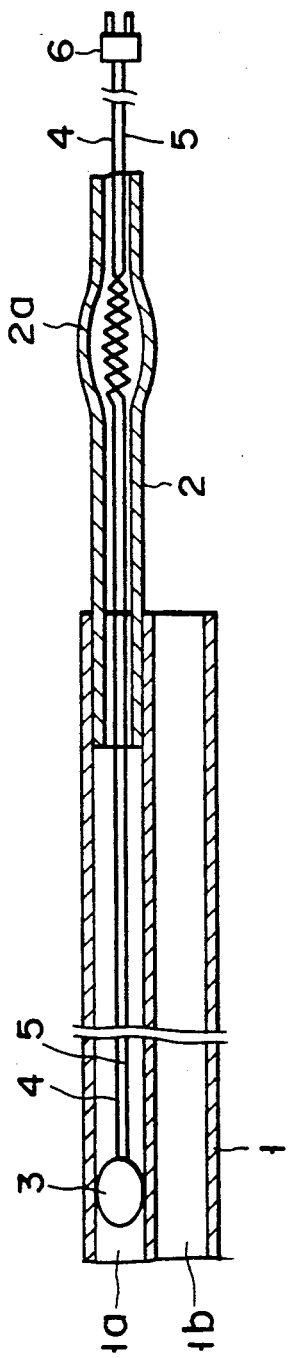
FIG. 3 is a sectional view of the main parts of an electrical wire-accommodating catheter according to still another embodiment of the present invention having an enlargement in part of an extension tube.

The present invention will now be explained with reference to specific embodiments.

FIG. 1 is a sectional view of the main parts of an electrical wire-accommodating catheter according to the present invention, comprising a catheter body 1 and an extension tube 2 connected to one end of the body. The catheter body 1 has a plurality of cavities 1a (maximum internal diameter 0.5 mm) and 1b (maximum internal diameter 1 mm), and a sensor 3 is inserted into the proximal end portion of one of them. Electrical wires made of, for example, copper wires of a diameter not greater than 0.1 mm are connected to the sensor 3 at their ends. An enlargement 1c of maximum internal diameter 1.7 mm, made by slightly widening the internal diameter is formed at the proximal end portion of the catheter body 1, and excess lengths of the wires 4 and 5 are coiled slack in this enlargement. The wires 4 and 5 are then led to the outside via an extension tube 2 of internal diameter 1.1 mm, and their proximal ends are connected to a connector terminal 6. Further, as shown in FIG. 1, the extension tube 2 has also an enlargement 2a of maximum internal diameter 2.5 mm made by partly widening the internal diameter of the intermediate part of the extension tube 2, and the wires 4 and 5 are also coiled in this portion.

In the embodiment of FIG. 1, there has been described the case where an enlargement is provided in both the catheter body 1 and extension tube 2, and excess lengths of the electrical wires 4 and 5 are accommodated slack these portions. If however it is possible to comply fully with the elongation of the catheter body 1 and the extension tube 2 by accommodating an excess of wire in either the catheter body or the extension tube, the enlargement may be provided in either the catheter body or the extension tube only. For example, the enlargement may be provided only in the catheter body 1 as shown in FIG. 2, or only in the extension tube 2 as shown in FIG. 3. It will of course be understood that if necessary, an enlargement may be provided at 2 or more positions. Moreover, if the material of the catheter body 1 and extension tube is polyvinyl chloride, it may suffice that excess lengths of the wires 4 and 5 are accommodated as slack, taking into account that a maximum elongation under external stress is assumed to be 80%. Needless to say, the excess lengths of the electrical wires can be suitably chosen depending on the material of the catheter body 1 and extension tube 2, including polyolefins, ethylene-vinyl acetate copolymer, polyvinyl chloride, nylon, polyurethane, silicone rubber and natural rubber which are generally used.

The enlargements 1c of catheter body 1 and 2a of extension tube 2 may be easily made in an extrusion molding process, for example, by adjusting a resin discharge amount, pull-down rate and air blow volume. Further, any desired means may be used to insert the coiled wire. It may for example easily be inserted by coiling it on a rod which ca be inserted into the catheter or extension tube, inserting the rod and coil into the catheter body 1 or extension tube 2, and then withdrawing only the rod.

Figure 4:
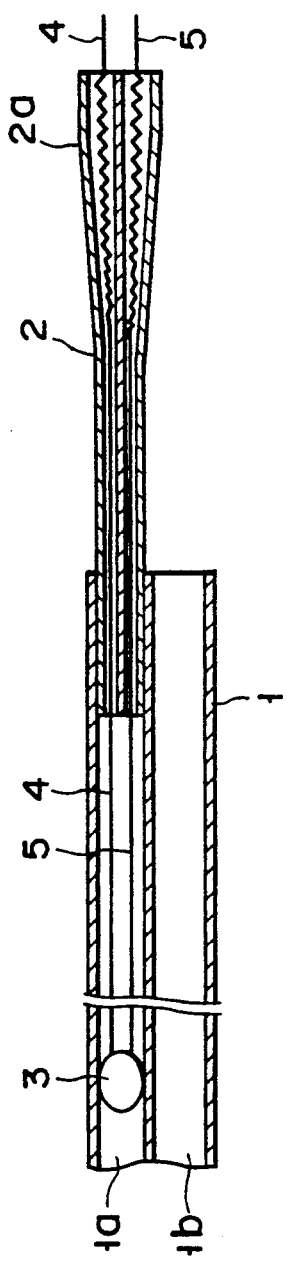
FIG. 4 is a sectional view of the main parts of an electrical wire-accommodating catheter according to still another embodiment of the present invention having an enlargement at the end of an extension tube having multiple cavities.

FIG. 4 shows another embodiment of the present invention. It differs from the embodiment of FIG. 1 in that the extension tube 2 has multiple cavities therein, the wires 4 and 5 being accommodated into each of these cavities separately; that an enlargement for accommodating an excess of slack wire is provided only in the extension tube 2; and that this enlargement 2a is provided at the end of the extension tube. In all other points, it is identical to FIG. 1.

Figure 5:
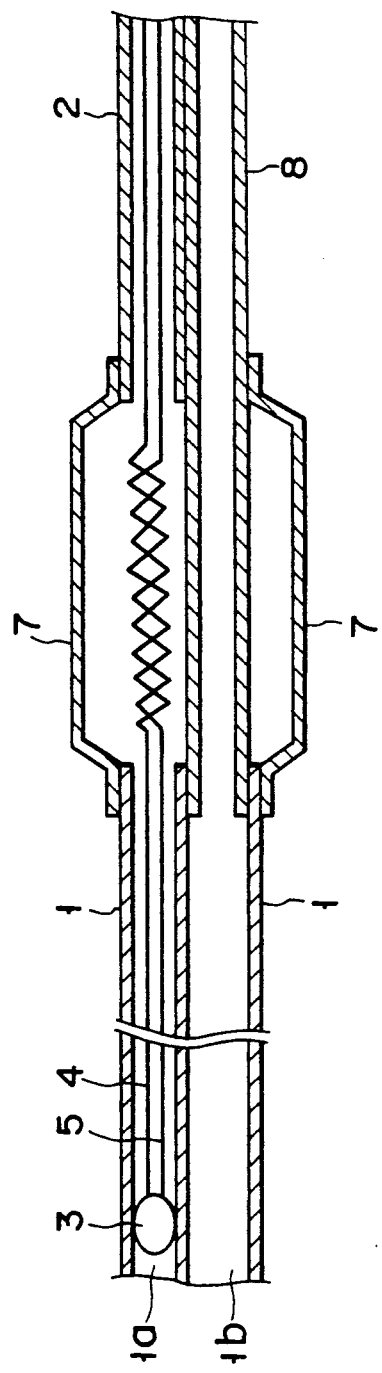
FIG. 5 is a sectional view of the main parts of an electrical wire-accommodating catheter according to still another embodiment of the present invention wherein the enlargement constitutes a connecting part between the catheter body and an extension tube.

FIG. 5 shows a further embodiment of the present invention wherein the enlargement constitutes a connecting body 7 of which one end is connected to catheter body 1, and the other end is connected to the extension tube 2 and a flowpath extension tube 8. The portions of the wires 4 and 5 arranged in the form of a coil can be accommodated in this connecting body 7. In addition to this connecting body 7, enlargements may also be provided in both catheter body 1 and extension tube 2, or in either of them, and in these cases may be provided at 2 or more positions if necessary.

We claim:

1. A catheter accommodating an electrical wire therein, comprising:
   an elongated catheter member having a plurality of elongated cavities provided therein, said cavities extending in a longitudinal direction of the elongated catheter member, said elongated catheter member being stretchable form a first length in an unstretched state to a longer length in a stretched state;
   a sensor arranged in one of said elongated cavities; and
   an elongated electrical wire arranged in said one of said cavities and electrically connecting to the sensor the length of said electrical wire extending along the length of said one of said cavities and having a length greater than said first unstretched length and being accommodated in said one of said cavities with slack, whereby an excess length of said electrical wire is accommodated in said one of said cavities;
   an enlargement formed in only a portion of the length of said one of said cavities; and
   substantially all of said excess length of said electrical wire with respect to the length of the elongated catheter ember in an unstretched state of the elongated catheter member being accommodated slack in said enlargement.

2. The catheter of claim 1, wherein;
   the elongated catheter member includes a catheter body and an extension tube connected to the catheter body;
   said enlargement comprising an internal diameter-enlarged portion formed in at least part of at least one of said catheter body and said extension tube; and
   said excess length of said electrical wire corresponding to a maximum elongation of said catheter body and extension tube is accommodated slack in said internal diameter-enlarged portion.

3. The catheter of claim 1, wherein:
   the elongated catheter member includes a catheter body, an extension tube, and a connecting body having one end which is connected to said catheter body and another end which is connected to the extension tube;
   said enlargement comprising an internal diameter-enlarged portion formed in at least one of said catheter body, said extension tube and said connecting body; and
   said excess length of said electrical wire corresponding to a maximum elongation of said catheter body and said extension tube is accommodated slack in the internal diameter-enlarged portion.

4. The catheter of claim 3, wherein:
   at least one of said catheter body and extension tube has said plurality of cavities therein; and
   wires are accommodated separately in each of said plurality of cavities.

5. The catheter of claim 1, wherein the length of excess electrical wire accommodated in said enlargement is not less than 10% of a maximum elongation of said catheter member.

6. The catheter of claim 1, wherein said excess length of electrical wire accommodated in said enlargement is in the form of a coil.

7. The catheter of claim 1, wherein:

said elongated catheter member comprises a catheter body having a distal tip portion and a proximal base portion;

said sensor is arranged in said distal tip portion of said catheter body; and said enlargement is formed in said proximal base portion of said catheter body.

8. The catheter of claim 1, wherein said sensor and said electrical wire are exclusively provided in said one of said elongated cavities which has said enlargement formed therein.

9. The catheter of claim 1, wherein said enlargement comprises an internal diameter-enlarged portion of said one of said cavities.

10. The catheter of claim 1, wherein said enlargement comprises an enlarged internal cross-sectional portion of said one of said cavities.

* * * * *

UNITED STATES PATENT AND TRADEMARK OFFICE
CERTIFICATE OF CORRECTION

PATENT NO. : 5,092,333
DATED : March 3, 1992
INVENTOR(S) : TSUCHIDA et al

It is certified that error appears in the above-identified patent and that said Letters Patent is hereby corrected as shown below:

TITLE PAGE:

Below inventors, insert the following:

--[73] Assignee: Terumo Kabushiki Kaisha, Tokyo, Japan--

In Section [30] Foreign Application Priority Data, insert the following:

--June 23, 1988 [WO] PCT Int'l. Appl.....PCT/JP88/00621--.

In Section [56] References Cited, insert the following under "Foreign Patent Documents":

```
54-83279     1979     Japan
54-36083     3/1979   Japan
59,174/69    2/1971   Australia
```

Signed and Sealed this

Twenty-fourth Day of August, 1993

Attest:

BRUCE LEHMAN

Attesting Officer    Commissioner of Patents and Trademarks